United States Patent [19]

Eggers

[11] Patent Number: 5,330,471
[45] Date of Patent: Jul. 19, 1994

[54] BI-POLAR ELECTROSURGICAL ENDOSCOPIC INSTRUMENTS AND METHODS OF USE

[75] Inventor: Philip E. Eggers, Dublin, Ohio

[73] Assignee: Hemostatic Surgery Corporation, Georgetown,

[21] Appl. No.: 877,704

[22] Filed: May 1, 1992

Related U.S. Application Data

[63] Continuation-in-part of Ser. No. 711,920, Jun. 7, 1991, abandoned.

[51] Int. Cl.$^5$ ............................................. A61B 17/38
[52] U.S. Cl. ......................................... 606/48; 606/32; 606/34; 606/39; 606/40; 606/41; 606/46; 606/49; 606/50
[58] Field of Search ................... 128/399, 402; 606/32, 606/34, 40–41, 48–52, 174, 170, 110–112

[56] References Cited

U.S. PATENT DOCUMENTS

| | | |
|---|---|---|
| 659,409 | 9/1900 | Mosher . |
| 1,586,645 | 6/1926 | Bierman . |
| 1,798,902 | 3/1931 | Raney . |
| 3,651,811 | 3/1972 | Hilderbrant et al. ............... 606/51 |
| 3,685,518 | 8/1972 | Beurle et al. . |
| 4,003,380 | 1/1977 | Wien ................................. 606/51 |
| 4,128,099 | 12/1978 | Bauer . |
| 4,232,676 | 11/1980 | Herczog .......................... 606/50 |
| 4,353,371 | 10/1982 | Cosman . |
| 4,370,980 | 2/1983 | Lottick . |
| 4,492,231 | 1/1985 | Auth ................................. 606/40 |
| 4,643,190 | 2/1987 | Heimberger . |
| 4,655,216 | 4/1987 | Tischer . |
| 4,669,471 | 6/1987 | Hayashi . |
| 4,671,274 | 6/1987 | Sorochenko . |
| 4,763,669 | 8/1988 | Jaeger . |
| 4,785,807 | 11/1988 | Blanch . |
| 4,819,633 | 4/1989 | Bauer et al. . |
| 4,848,337 | 7/1989 | Shaw et al. . |
| 4,887,612 | 12/1989 | Esser et al. . |
| 4,944,093 | 7/1990 | Falk . |
| 4,977,900 | 12/1990 | Fehling et al. . |
| 4,985,030 | 1/1991 | Melzer et al. . |
| 5,009,656 | 4/1991 | Reimels . |
| 5,085,659 | 2/1992 | Rydell . |
| 5,147,357 | 9/1992 | Rose et al. . |

FOREIGN PATENT DOCUMENTS

| | | |
|---|---|---|
| 0210125 | 1/1987 | European Pat. Off. . |
| 0341446 | 11/1989 | European Pat. Off. . |
| 2355521 | 1/1978 | France .................................. 606/52 |
| 2536924 | 6/1984 | France . |
| 2647683 | 12/1990 | France . |
| 342619 | 7/1971 | U.S.S.R. . |
| 575103 | 10/1977 | U.S.S.R. . |
| 2037167 | 7/1980 | United Kingdom . |
| 2066104 | 8/1981 | United Kingdom . |
| 2161082 | 1/1986 | United Kingdom . |

OTHER PUBLICATIONS

"The Cauitron Bipolar Coagulator", 1979, Cauitron Surgical Systems.
The Lancet, "New Inventions", Oct. 24, 1959, J. D. K. Burton, pp. 650–651.
Copy of UK Pat. Appln. 2 133 290 provided as translation of French Pat. Appln. 2 536 924.
Corson, S. L., "Two new laparoscopic instruments: Bipolar sterilizing forceps and uterine manipulator," Medical Instrumentation, vol. 11, Jan.-Feb. 1977.

Primary Examiner—Randall L. Green
Assistant Examiner—P. Zuttarelli
Attorney, Agent, or Firm—Nicola A. Pisano

[57] ABSTRACT

Endoscopic surgical instruments are provided that have bipolar electrodes on opposing movable members for passing a high frequency current through tissue for simulataneously severing or manipulating the tissue and causing hemostasis of the tissue. An electrically insulating material is interposed between the movable members so that the electrodes are spaced apart from 0.002 to 0.050 inches and the current passes between the opposing electrodes through the tissue. Methods of endoscopically achieving hemostasis while simultaneously, manipulating and cutting tissue are also provided. Use of a constant voltage high frequency power supply to deliver current to the tissue to cause hemostasis is described in conjunction with those methods.

27 Claims, 7 Drawing Sheets

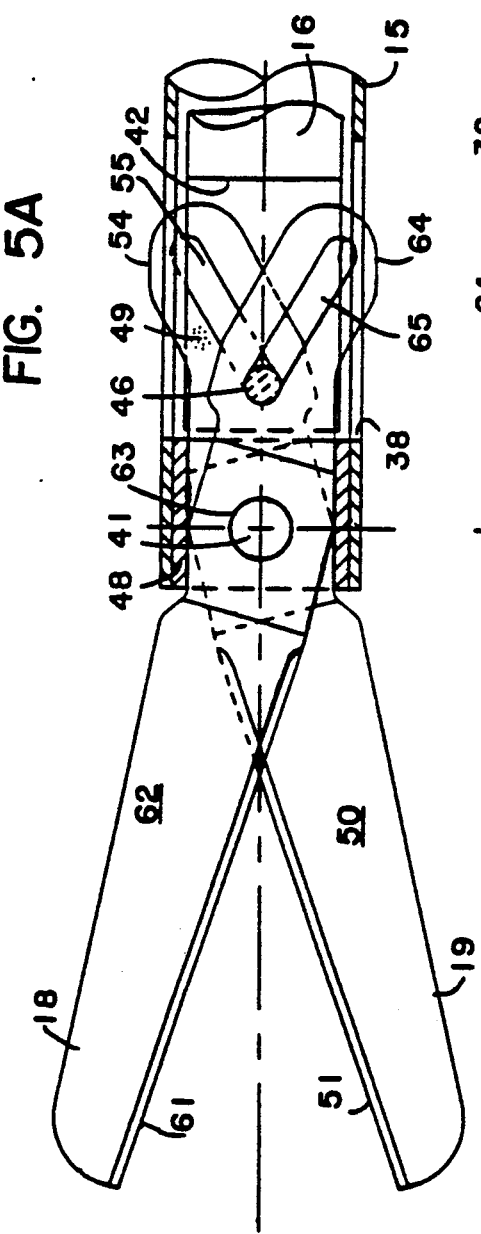
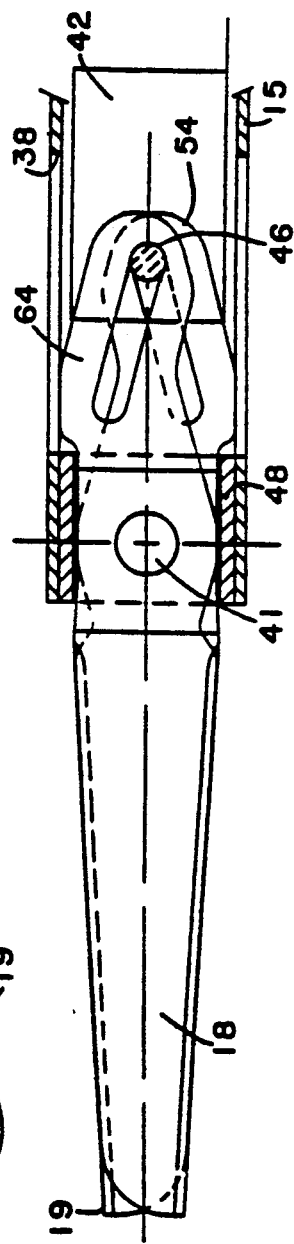
FIG. 5A
FIG. 5B

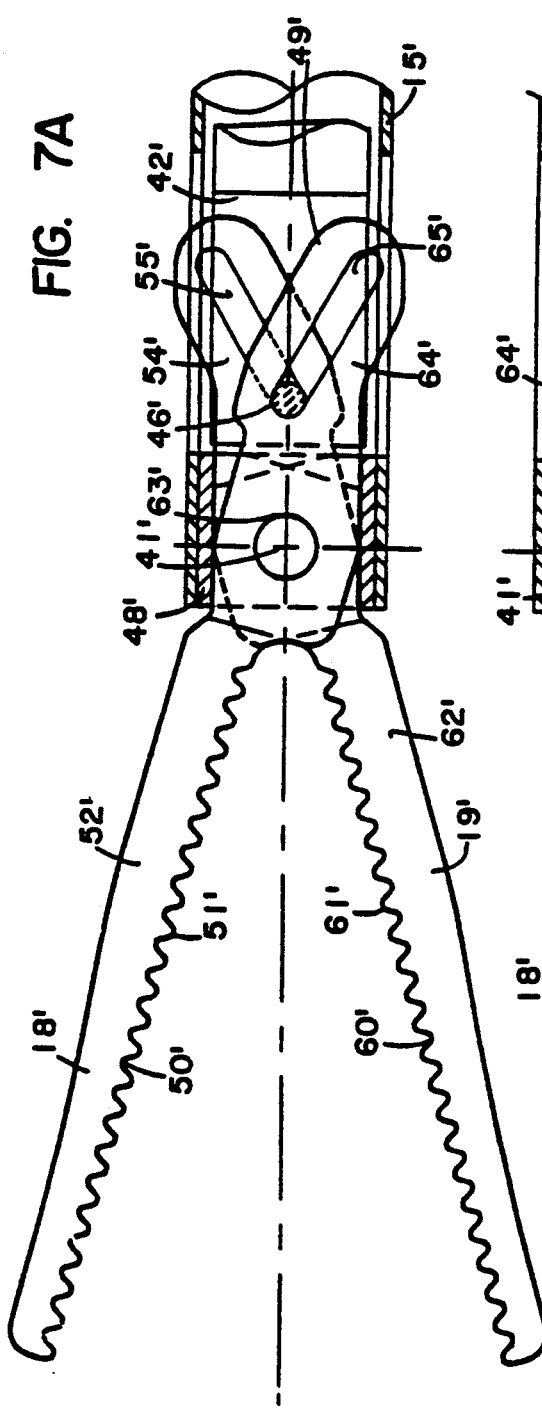
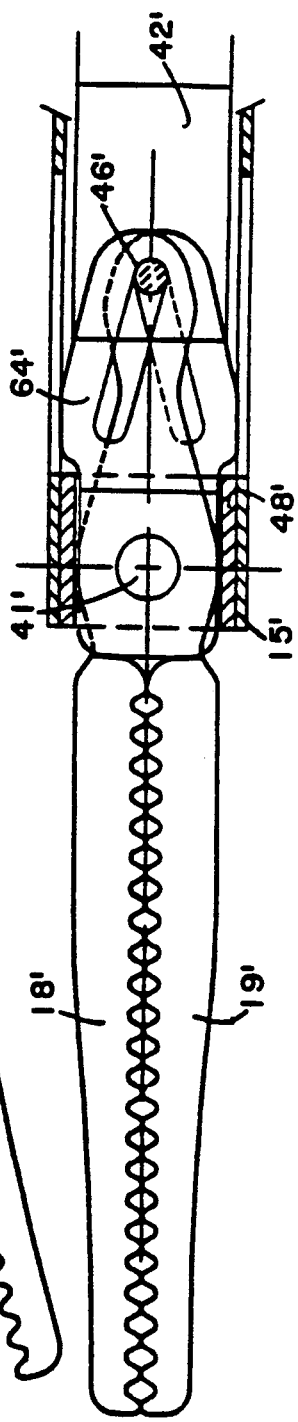

BI-POLAR ELECTROSURGICAL ENDOSCOPIC INSTRUMENTS AND METHODS OF USE

This application is a continuation-in-part of commonly assigned and copending U.S. patent application Ser. No. 07/711,920, filed Jun. 7, 1991 now abandoned.

This invention relates to hemostatic electrosurgical instruments, and particularly to improved bi-polar electrosurgical instruments for manipulating and causing hemostasis of tissue during endoscopic surgical procedures.

BACKGROUND OF THE INVENTION

In "open" surgical procedures, the surgeon gains access to work inside the body by cutting large incisions through the body wall, then stretching the overlying tissue apart to provide visibility and room to manipulate his hands and instruments. Vital structures are generally held away from the surgical site and shielded from instruments by being covered with cloth pads. The surgeon can touch and manipulate the tissues. As the surgeon manipulates, cuts and dissects tissues, he controls the resultant bleeding by blotting or suctioning away the accumulating blood, enabling him to see the bleeding vessels and clamp and tie them off.

The creation of a large opening in the patient's body tissue greatly increases the risk of surgery to the patient's health, by increasing the probability of complications. Those complications can arise not only from treatment of the target tissue, i.e., that tissue necessitating the surgery, but also from the trauma caused to adjacent tissue in creating an opening providing the surgeon with access to the target tissue. Once the internal tissue is operated upon, the surgeon faces the time-consuming task of closing up the surgical site. In addition, the patient may require extensive post-operative care and an extensive hospital stay.

Development of the endoscope, a miniaturized television camera that is inserted through a puncture wound in the body wall to provide a video image of the inside of the body cavity, has enabled surgeons to perform surgery using specially designed surgical instruments that are inserted through other small puncture wounds. Some previously known devices have been constructed that enable a surgeon to operate on internal tissue while viewing manipulation of the instrument through an endoscope. One such device is described in Falk, U.S. Pat. No. 4,994,024. Such previously known endoscopic instruments have several disadvantages, especially the inability to effectively stem blood flow from incised tissue.

Endoscopic surgery no longer requires cutting a large gaping incision through the body wall, and permits patients to undergo some major surgeries practically pain-free, with little or no post-operative hospital stay. However, in performing endoscopic surgery the surgeon forgoes manual access to the tissues being operated upon. In doing so, he gives up his traditional means of controlling bleeding by clamping and tying off transected blood vessels. Consequently, in endoscopic surgery it is important that tissues that are cut must not bleed.

Hemostatic surgical techniques are known for reducing the bleeding from incised tissue during open surgical procedures, i.e., where overlying body tissue is severed and displaced to gain access to internal organs. Such techniques include electrosurgery, that is, passing a high frequency or radio frequency current through the patient's tissue between two electrodes for cutting and coagulating the blood vessels contained within the tissue. The current passing through the tissue causes joulean (ohmic) heating of the tissue as a function of the current density and the resistance of the tissue through which the current passes. This heating dehydrates the tissues and denatures the tissue proteins to form a coagulum which seals bleeding sites, so that the body's own collagen is reformed as a glistening white layer on the cut surface, sealing the tissues against bleeding.

Heretofore, endoscopic electrosurgical techniques have been limited primarily to monopolar devices. Previously known monopolar electrosurgical instruments employ a small electrode at the end of a handle in the surgeon's hand and a large electrode plate beneath and in contact with the patient. Only one of the two electrodes required to complete the electrical circuit is manipulated by the surgeon and placed on or near the tissue being operated on. The other electrode is the large plate beneath the patient. A power supply impresses high frequency voltage spikes of thousands of volts between the two electrodes of the electrosurgical instrument, sufficient to cause arcing from the small operating electrode the surgeon holds to the most proximate tissues, then through the patient to the large electrode plate beneath the patient. In the patient, the electrical current becomes converted to heat; hottest in the tissues immediately below the small hand-held electrode where the currents are most concentrated. Devices, such as the forceps Model No. A5261, and electrode Model No. A5266, available from Olympus Corporation Medical Instrument Division, Milpitas, Calif., are representative of such monopolar instruments.

A principal disadvantage of monopolar electrocautery is that current flows completely through the patient. These high voltage electrical currents may arc from the small electrode to nearby non-targeted vital structures, or may follow erratic paths as they flow through the patient's body, thereby causing damage to tissues both near and at some distance from the electrode.

While monopolar devices have proven useful in open surgical procedures, where the surgeon is able to view the effects of the current arc, the problems encountered in open surgical procedures become even more important in endoscopic surgical applications. In particular, when using a monopolar device endoscopically, the surgeon's view of the electric arc generated by the instrument is restricted by the limited field of view provided by the endoscope. Consequently, aberrant current arcs—the existence of which the surgeon may not even be aware—can cause deep tissue necrosis and inadvertent damage to adjacent tissue masses.

The foregoing limitation has proved especially dangerous for surgeries performed in the abdomen, and in the vicinity of the peritonea and bowel wall. Practical experience has established that aberrant current arcs generated by endoscopic monopolar devices can cause perforation of the adjacent bowel wall when used on abdominal tissue masses. While such damage typically is not apparent to the surgeon during the procedure, it may later be manifested as peritonitis, which results in death in as many as 25% of all such cases.

Bipolar electrosurgical devices for open surgical procedures are known to enable the surgeon to obtain hemostasis in precise local areas without also heating and causing undesirable trauma to adjacent tissue. Bipolar devices have two electrodes closely spaced together so that current flow is confined to the tissue disposed between the electrodes. Heretofore, such instruments have had limited use in endoscopic applications because of the inherent problem of electrically isolating the high voltage electrodes while providing an instrument small enough for use with conventional trocar tubes—typically 5 to 10 mm in diameter. One such device is described in Tischer U.S. Pat. No. 4,655,216. The complicated structure of the device described in that patent illustrates the difficulty encountered in providing the requisite isolation of the electrodes. A second such device is the Olympus Model O5127 bipolar endoscopic forceps, available from Olympus Corporation Medical Instrument Division, Milpitas, Calif.

A further disadvantage inherent in all previously known monopolar and bipolar electrosurgical devices is that of coagulum buildup on the working surfaces of the device. Previously known power supplies used in electrosurgical applications have generally provided high voltage-low current power outputs, which poorly match the impedance of the tissue over the range of conditions typically encountered in electrosurgery. This mismatch, in combination with the arcing characteristic of previously known instruments, leads to charring of the tissue and excessive coagulum buildup on the instrument surfaces.

Yet another difficulty encountered in endoscopic surgery is the limited range of motion available to the surgeon at the surgical site. In particular, because of the relatively small incision through which the instruments are inserted for endoscopic procedures, the surgeon's range of movement of the instrument is greatly restricted.

It would therefore be desirable to provide bipolar electrosurgical instruments for hemostatically severing or manipulating tissue in endoscopic surgical procedures that overcome these disadvantages of such previously known instruments. Such instruments would enable a large number of operations to be carried out endoscopically, thereby reducing the need and risk of open surgical procedures.

SUMMARY OF THE INVENTION

In view of the foregoing, it is an object of the present invention to provide improved endoscopic surgical instruments, the existence of which will expand the field of endoscopic surgery. In particular, the existence of instruments providing heretofore unavailable functions, ease of use, and enhanced safety will encourage the conversion of a number of surgeries—now carried out as open procedures—to endoscopic procedures. Such conversion from open to endoscopic surgeries will reduce the risk of surgery to the patient, reduce the trauma to adjacent tissue from the surgery, and enable faster post-operative recovery.

It is, therefore, an object of this invention to provide bipolar electrosurgical instruments for endoscopic surgical procedures that have a simple structure, yet provide the necessary electrical isolation of the bipolar electrodes. The bipolar devices constructed in accordance with the present invention confine current flow to the tissue immediately adjacent to the electrodes of the instrument. Thus, these devices significantly reduce the likelihood of creating aberrant current arcs that can perforate the peritonea or other adjacent tissue. The overall safety of endoscopic procedures is thereby enhanced, permitting a larger number of surgeries to be performed endoscopically.

It is another object of the present invention to provide bipolar endoscopic instruments which experience little sticking or coagulum buildup during extended use. In accordance with the present invention, endoscopic bipolar instruments are employed in conjunction with power supplies providing load-independent substantially constant voltage output. Voltage and current ranges are provided that significantly reduce coagulum buildup and charring of tissue.

It is another object of this invention to provide bipolar electrosurgical instruments that provide the surgeon with a high degree of maneuverability of the instrument once it is located at the surgical site. The instrument constructed in accordance with the principles of this invention therefore includes means for rotating the working end of the instrument while it is positioned at the surgical site.

These and other objects are accomplished in accordance with the principles of the present invention by providing bipolar electrosurgical instruments having an elongated barrel for insertion through a trocar tube at the patient's skin, a working end disposed on the distal end of the elongated barrel, and handle members for actuating the instrument. Means are provided near the proximal end of the barrel for rotating the working end of the instrument. The instrument includes means for connecting the instrument to a power supply to energize the electrodes at the working end.

Bipolar instruments constructed in accordance with the present invention have a working end that comprises bipolar electrodes and movable members capable of performing any of a number of functions. A layer of insulation is provided on one or both of the mating surfaces of the movable members to maintain electrical isolation of those components. A working end constructed in accordance with the present invention may comprise a scissors-like cutting instrument which simultaneously causes hemostasis of tissue and mechanically severs that tissue in a continuous manner, a dissector-like instrument for grasping and achieving hemostasis of tissue, or a dissector for blunt dissection, which hemostatically separates tissue.

In a first embodiment, the movable members of the working end comprise scissor members having opposing mating surfaces. Electrodes associated with the scissor members conduct high frequency current to tissue to coagulate the blood vessels extending through the tissue while cutting edges of the scissor members mechanically sever the tissue. A layer of insulating material is disposed on at least one of the mating surfaces of the scissor members so that the electrically active portions of the scissor members do not contact each other at any point during operation of the instrument. Thus, current flows through tissue between the scissor members, but short circuits, which would terminate hemostasis, do not occur. With this arrangement, hemostasis and cutting occurs in a continuous manner along tissue disposed between the scissor members, thereby providing a smooth and precise surgical cut.

Another embodiment of the invention comprises an endoscopic hemostatic dissector, wherein the movable members comprise opposing jaws for simultaneously grasping and causing hemostasis of the tissue. Like the first embodiment, the jaw members include shank portions forming opposing mating surfaces. A layer of insulating material is disposed on at least one of these mating surfaces so that electrically active portions of the members do not contact each other during operation of the instrument.

The movable members of either embodiment may be curved so that the tips of the members lie in a plane parallel to, and separate from, the longitudinal axis of the elongated barrel. This feature enhances the surgeon's view of the working end of the instrument, thereby providing greater precision in manipulating the tissue at the operative site.

The present invention also includes methods of endoscopically using bipolar electrosurgical instruments to simultaneously grasp or mechanically sever tissue while thermally reforming the collagen of the tissue to seal the tissue against bleeding. For endoscopically performing surgery on a patient's internal tissue using a bipolar electrosurgical instrument in combination with a power supply having a selectable substantially constant voltage load-independent output, the instrument having an elongated barrel, a working end comprising electrodes, and means for actuating the working end, the methods include the steps of:

(a) connecting the electrodes of the bipolar electrosurgical instrument to the power supply;

(b) incising the patient's tissue with a trocar or similar device to create a small opening;

(c) inserting the working end and elongated barrel of the bipolar electrosurgical instrument through a trocar tube so that the working end is disposed proximal to the internal tissue; and (d) operating the actuating means to simultaneously manipulate and cause hemostasis of the tissue.

Further steps of the methods include the step of setting the power supply to provide a voltage across the electrodes in the range of 10 to 120 volts (RMS) and a frequency in the range of 100 kHz to 2 MHz. The methods further include the use of alternating-current voltage waveforms having a crest factor—ratio of peak voltage to root-mean-square (RMS) voltage—near unity.

BRIEF DESCRIPTION OF THE DRAWINGS

The above and other objects and advantages of the invention will be apparent upon consideration of the following detailed description, taken in conjunction with the accompanying drawings, in which like reference numerals refer to like parts throughout, and in which:

FIGS. 5A and 5B show, respectively, open and closed enlarged cross-sectional views of the working end of the instrument shown in FIG. 2;

FIGS. 7A and 7B, respectively, are cross-sectional views, similar to FIGS. 5A and 5B, showing a dissector embodiment of the working end of the present invention.

DETAILED DESCRIPTION OF THE INVENTION

Figure 1:
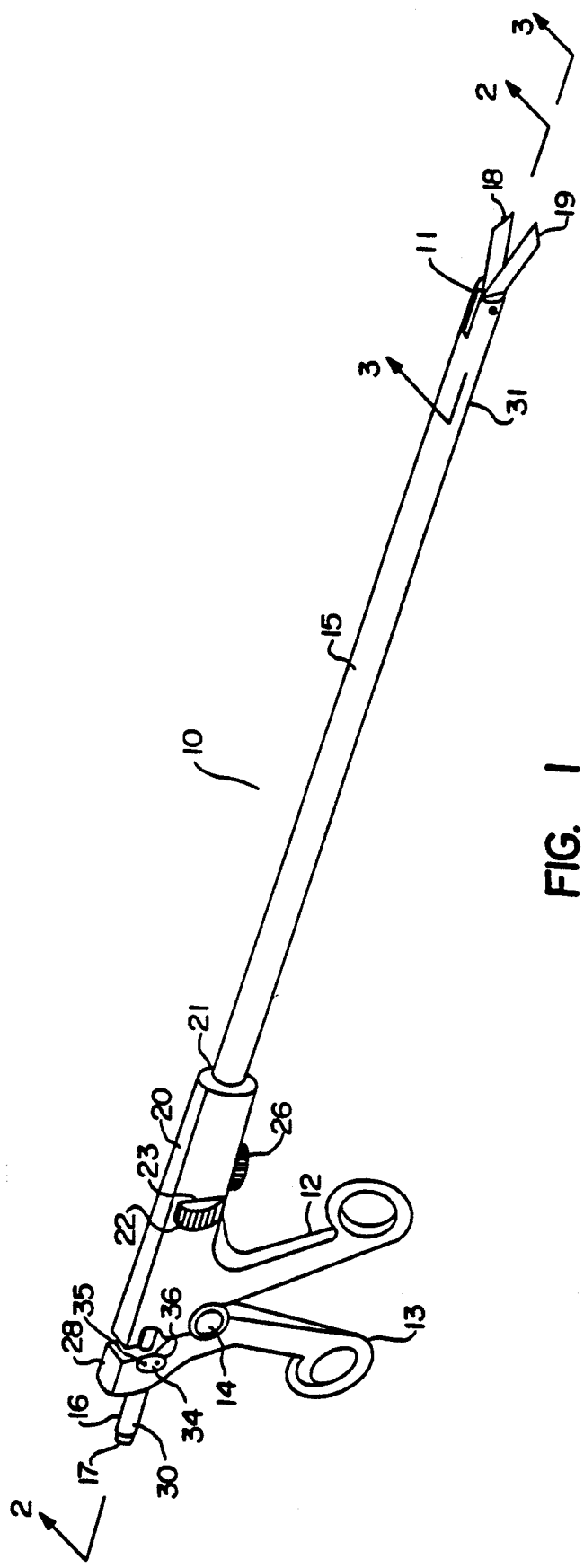
FIG. 1 is an elevated perspective view of an illustrative embodiment of the instrument of the present invention.
Figure 2:
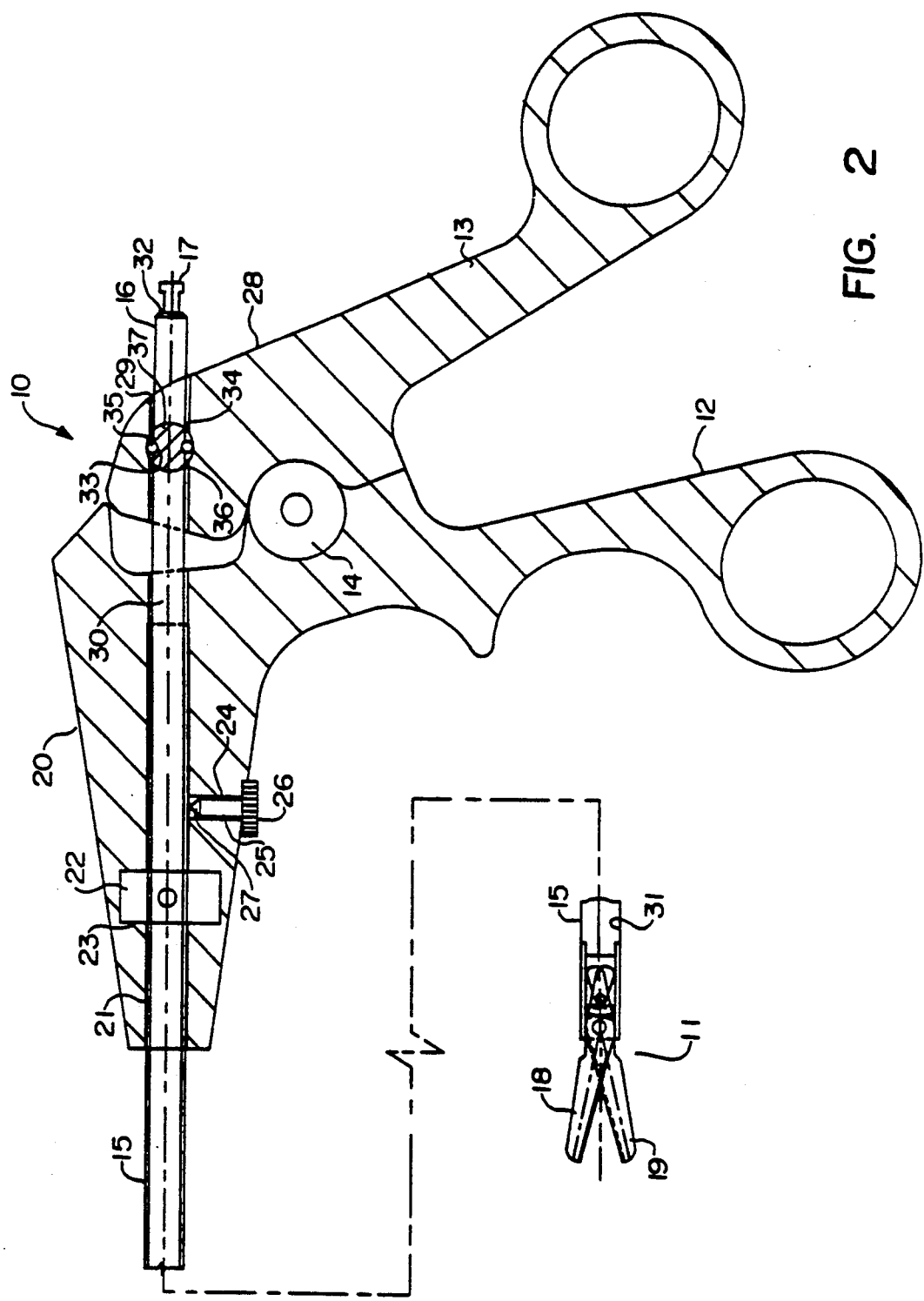
FIG. 2 is an elevation cross-sectional side view of the instrument taken along the line 2—2 of FIG. 1, in which an intermediate portion of the elongated barrel has been omitted for clarity.

Referring to FIGS. 1 and 2, a bipolar electrosurgical instrument 10 for performing endoscopic surgical procedures is described. While an instrument constructed in accordance with the principles of the present invention may include any of a variety of severing or grasping members at its working end 11, the illustrative embodiment of FIGS. 1 and 2 includes scissor-like shearing members for simultaneously severing and causing hemostasis of a patient's tissue.

Instrument 10 includes actuating means comprising handle members 12 and 13 joined for relative movement at pivot 14, tubular elongated barrel 15, and working end 11. Drive rod 16 disposed in elongated barrel 15 has electrical terminals 17 that are connected to movable members 18 and 19 of working end 11 to provide an electrical potential therebetween.

Handle member 12 has a pistol-like configuration, including a body portion 20 having a longitudinal bore 21 and a portion defining a hole for one or more fingers. Handle member 12 may be made of a light-weight rigid material, for example cast aluminum. Elongated barrel 15 comprises a tube having a proximal end mounted in body portion 20 and a distal portion forming part of working end 11. The proximal end of elongated barrel 15 is mounted in bore 21 of body portion 20 so that elongated barrel 15 can be rotated about its longitudinal axis. Elongated barrel 15 may consist of a rigid structural material, for example a stainless steel alloy, e.g., SS 304, and may include a coating of abherent material, such as Teflon, on its exterior surface.

Knurled rotation knob 22 is mounted on a portion of elongated barrel 15 disposed in body portion 21, so that it projects through slots 23 intersecting bore 21 of body portion 20. Rotation of knurled knob 22 causes elongated barrel 15 to rotate about its longitudinal axis, thereby also rotating working end 11.

Body member 20 has bore 24 communicating with bore 21 so that set screw 25 disposed in bore 24 engages elongated barrel 15 substantially perpendicularly to the longitudinal axis of the barrel. Set screw 25 has locking knob 26 at one end and teat 27 at the other end to engage elongated barrel 15. Rotation of locking knob 26 may impose a load on elongated barrel 15 to establish a threshold torque for rotating knurled rotation knob 22. Alternatively, locking knob 26 may be rotated so that teat 27 of set screw 25 effectively locks elongated barrel 15 in a given angular orientation, and against further rotation.

Handle member 13 has a lower portion defining a finger or thumb hole and an upper portion 28 having longitudinal bore 29. Longitudinal bore 29 aligns with longitudinal bore 21 in body portion 20 of handle member 12 when handle members 12 and 13 are joined for relative movement at pivot 14. Handle member 13 comprises a similar material as handle member 12, e.g., a cast aluminum alloy.

Drive rod 16 has a proximal end 30 disposed within elongated barrel 15 and a distal end 31 engaged with working end 11. Proximal end 30 of drive rod 16 has electrical terminals 17 projecting from its endface 32, and a portion adjacent to endface 31 that defines a semicircular groove 33. Because drive rod 16 has a high electrical potential relative to handle members 12 and 13 when electrical terminals 17 are connected to a power supply, drive rod 16 is electrically insulated from handle member 13 and elongated barrel 15 by a coating of electrically insulating material disposed on the exterior surface of drive rod 16.

Groove 33 of drive rod 16 is captured in insulating disk 34 between insulating pins 35. Insulating disk 34 seats in circular aperture 36 in upper portion 28 of handle member 13. Insulating disk 34 may comprise a high strength plastic, such as, Ultem (a proprietary plastic of the General Electric Company, Fort Wayne, Ind., fabricated from polyethermide), or a ceramic material. Longitudinal bore 37 extends through insulating disk 34 in alignment with longitudinal bore 29 of upper portion 28, for accepting proximal portion 30 of drive rod 16. Insulating disk 34 includes a pair of bores that perpendicularly intersect bore 37, the pair of bores accepting insulating pins 35. Insulating disk 34 is capable of angular movement in circular aperture 36, when handle member 13 rotates relative to handle member 12 about pivot 14.

Insulating pins 35, which may comprise a sturdy electrically insulating material such as ceramic or anodized aluminum, engage groove 33 in drive rod 16 so that the drive rod 16 is capable of rotating about its longitudinal axis, but cannot move transversely with respect to insulating pins 35. Accordingly, drive rod 16 is mounted to handle member 13 for rotation about its longitudinal axis in insulating pins 35 and for transverse motion with respect to handle member 12 by virtue of angular movement of insulating disk 34 in aperture 36.

Figure 3:
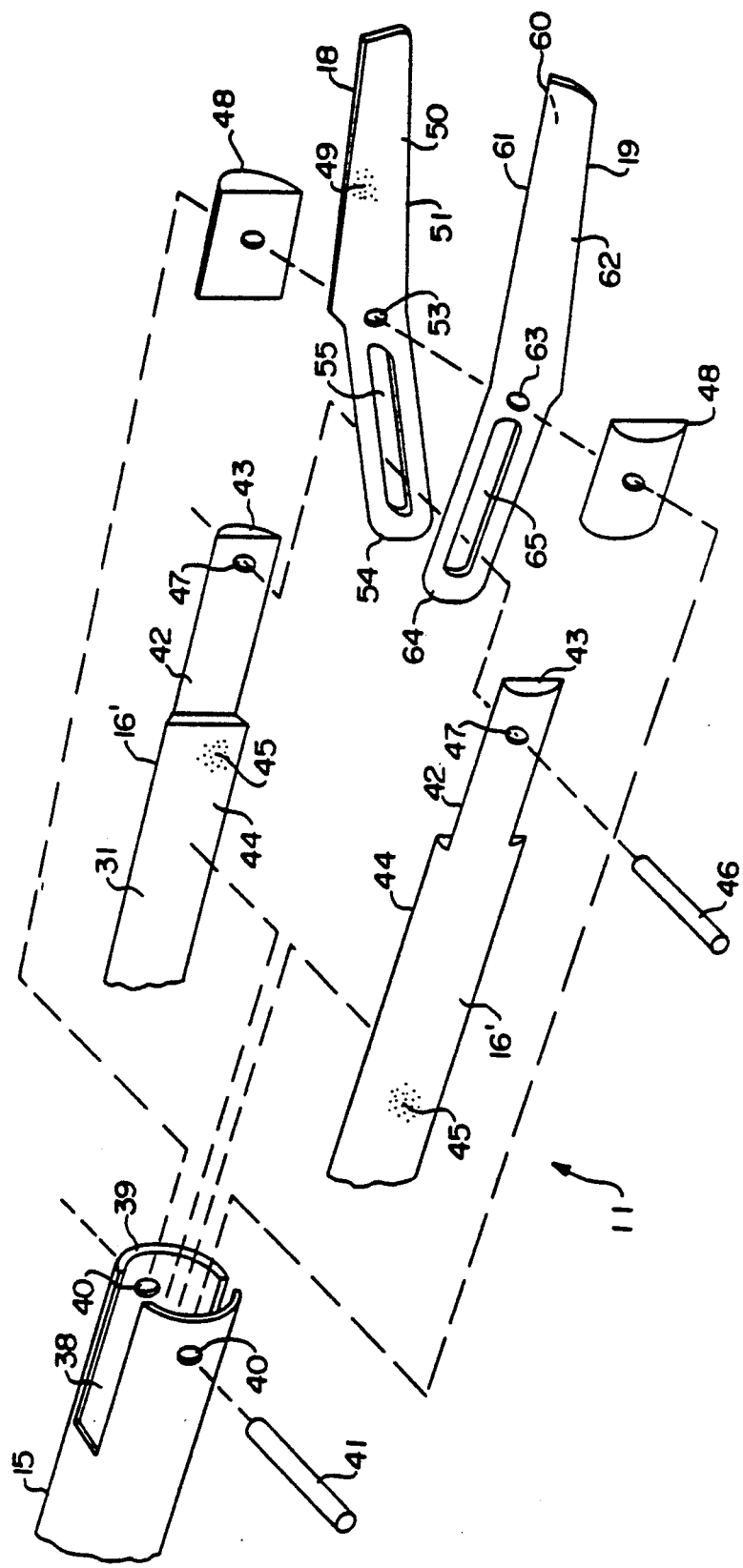
FIG. 3 is an exploded perspective view of the working end of the instrument taken along line 3—3 of FIG. 1.

Referring now to FIG. 3, a scissors-like embodiment of working end 11 is described. The distal end of elongated barrel 15 has diametrically opposed U-shaped slots 38 extending proximally from distal endface 39. Apertures 40 in the distal end of elongated barrel 15 are aligned across the diameter of the barrel to accept insulating pivot pin 41.

Proximal end 31 of drive rod 16 comprises semi-circular halves 16' each half 16' having an indentation 42 extending inward from its distal endface 43. Indentations 42 of halves 16' oppose each other to create a slot in the distal end of drive rod 16 within which the shanks of the movable members of working end 11 are disposed. Halves 16' have layer 45 of insulating material disposed on contacting surfaces 44, so that no current passes through those contacting surfaces. Layer 45 of insulating material also covers the outer surfaces of drive rod halves 16' to provide electrical insulation between drive rod 16 and elongated barrel 15. No insulation is provided on the interior surfaces of indentations 42, so that the interior surfaces of indentations 42 are in electrical contact with the shanks of the movable members. Insulating drive pin 46 extends through apertures 47 near the endfaces 43 of halves 16'.

Figure 4:
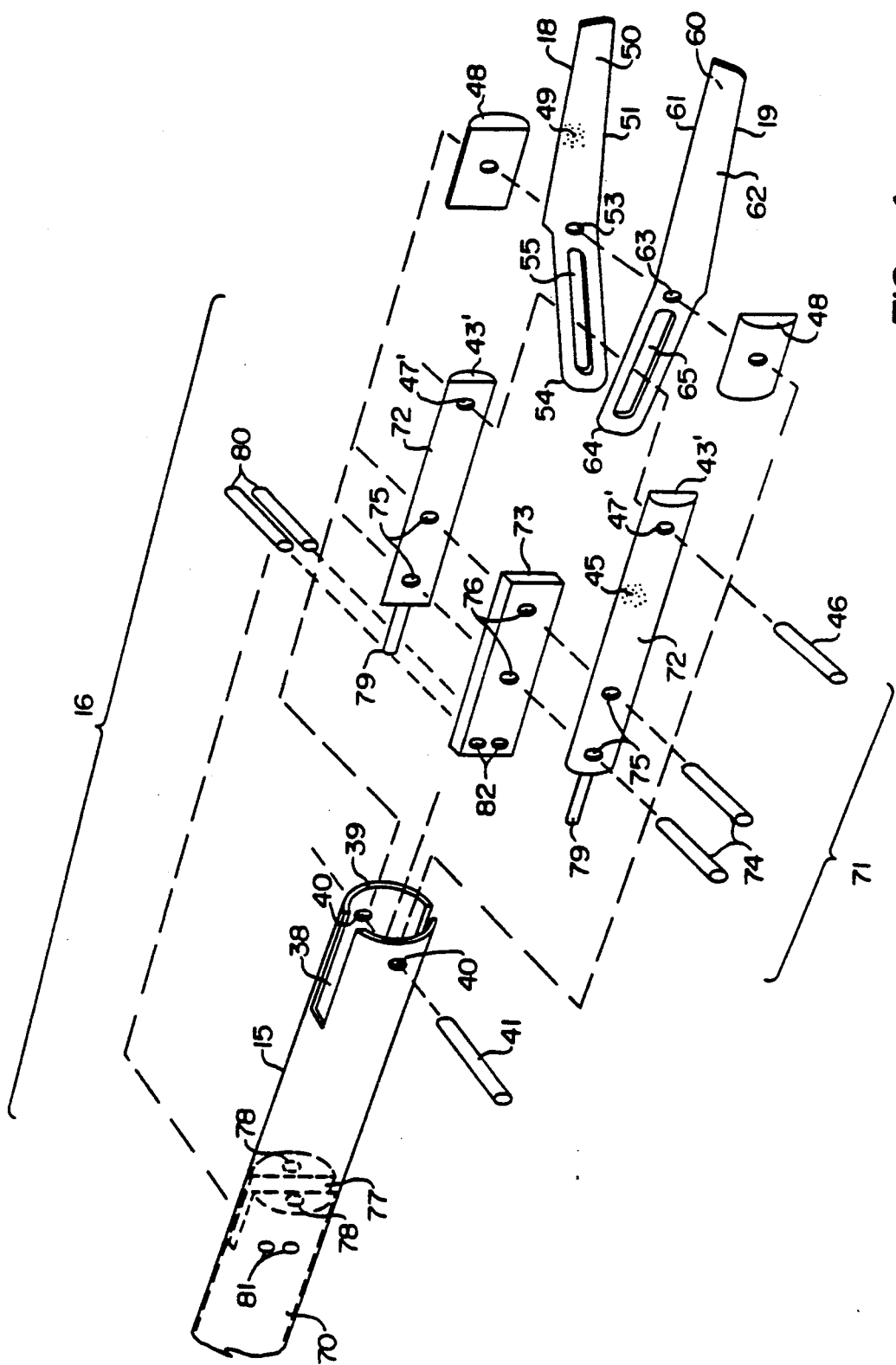
FIG. 4 is an exploded perspective view, similar to FIG. 3, of an alternate embodiment of the working end of the instrument.

An alternative embodiment of the drive rod is illustrated in FIG. 4, wherein drive rod 16 comprises drive member 70 carrying electrode assembly 71. Electrode assembly 71 in turn comprises semi-circular electrode halves 72 separated by insulating strip 73. Insulating strip 73 extends from the distal end of drive member 70 to a position near the shanks of the movable members to form a slot in the end of drive rod 16 for accepting the shanks of the movable members of working end 11. The inner surfaces of electrode halves 72 need not include a layer of insulating material, because insulating strip 71 serves to electrically isolate the electrode halves from each other.

The outer surfaces of electrode halves 72 are coated with an abrasion-resistant electrically insulating material 45' that electrically isolates the electrode halves from elongated barrel 15. Insulating material 45' may comprise, for example, Teflon or polyimide. Insulating drive pin 46 extends through apertures 47' located near the distal endfaces 43' of the electrode halves, as in the previously described embodiment.

Still referring to FIG. 4, electrode halves 72 are affixed to either side of insulating strip 73 by insulating pins 74. Insulating pins 74 extend through apertures 75 in electrode halves 72 and apertures 76 in insulating strip 73, respectively. Insulating pins may comprise a sturdy electrically insulating material, for example, ceramic or anodized aluminum.

The proximal end of insulating strip 73 is inserted into slot 77 in the distal end of drive member 70. In this embodiment, drive member 70, which comprises the major portion of drive rod 16, may comprise a sturdy electrically insulating material, such as Teflon or nylon. Drive member may then be formed, for example by extrusion, having two bores 78 to accept electrical connectors 79 projecting from the proximal faces of electrode halves 72. Bores 78 may then contain electrical leads that connect electrode halves 72 to electrical terminals 17 projecting from the proximal end of drive rod 16.

The proximal end of insulating strip 73 is affixed to the distal end of drive member 70 by pins 80. Pins 80 extend through apertures 81, provided for that purpose adjacent the slot 77 in drive member 70, and apertures 82 in insulating strip 73, respectively. Pins 80 comprise a sturdy electrically conducting or insulating material, inasmuch as pins 80 do not form a part of the electrical circuit of instrument 10. Thus, pins 80 may comprise, for example, either stainless steel or alumina.

For the illustrative embodiment shown in FIGS. 1-5, working end 11 of instrument 10 includes first and second members 18 and 19. First and second members 18 and 19 comprise scissor halves pivotally connected by insulating pivot pin 41. Tube insulator halves 48 are disposed adjacent to the exterior surfaces of members 18 and 19 to electrically insulate those members from elongated barrel 15. Insulating pivot pin 41 has its ends flush with the outer surface of elongated barrel 15 and extends, from side to side, through a first tube insulator half 48, members 18 and 19, and a second tube insulator half 48.

Insulating pivot pin may comprise an electrically insulating metallic pin, e.g., anodized aluminum, having its ends deformed by peening. Alternatively, insulating pivot pin 41 may comprise a rod-like member having a threaded recess at either end to accept a screw. The screws engage the threaded recesses and permit an adjustable compressive load to be applied to elongated barrel 15, and hence members 18 and 19.

Members 18 and 19 include, respectively, shearing surfaces 50 and 60, cutting edges 51 and 61, exterior surfaces 52 and 62, apertures 53 and 63, and shank portions 54 and 64. A thin layer 49 of insulating coating is provided on one or both of the opposing mating surfaces of members 18 and 19, including one or both of the shearing surfaces 50 and 60, and one or both of the mating surfaces of the shank portions 54 and 64.

Members 18 and 19 are configured to constitute the individual electrodes of a bipolar electrode instrument, as described in copending and commonly assigned U.S. patent application Ser. No. 07/877,703 filed May 1, 1992 the disclosure of which is incorporated herein by reference. That application describes a first family of embodiments wherein the opposing scissor halves are made of an electrically conducting material and serve as both the electrodes and shearing surfaces. That application also describes a second family of embodiments wherein the opposing scissor halves are made of an electrically insulating material and have electrically conductive portions disposed on the exterior surfaces of the scissor halves.

For the scissors-like embodiment of the working end shown in FIGS. 1-5, members 18 and 19 may be constructed of metallic alloys that offer good electrical conduction, adequate hardness and tensile strength sufficient to allow the members to be oriented toward each other to effect adequate wiping at the cutting edges. Materials having these characteristics include stainless steel, e.g., 301, 302, 304 and 316, martensitic stainless steels, e.g. 410, 420, 430 and 440, and precipitation hardened steels, e.g., 17-4PH and 17-7PH alloys. The use of such materials permit members 18 and 19 to be formed by numerous methods, including forging followed by machining, die casting, metal injection molding, and electrodischarge machining (EDM) cut-out of the features.

Layer 49 of insulating coating covers the inside face of one or both of cutting edges 51 and 61, so that the cutting edges are electrically isolated from each other. Thus, current flows between exterior surfaces 52 and 62 of members 18 and 19 in the region near cutting edges 51 and 61, while ensuring that members 18 and 19 do not electrically contact each other within the range of the cutting or opening motion of the members. Consequently, hemostasis of tissue occurs at a location just in advance of the cutting point while cutting edges 51 and 61 simultaneously sever the hemostatically heated tissue, as described in the above-referenced U.S. patent application Ser. No. 07/877,703.

Because shank portions 54 and 64 move through a range of motion wherein the opposing mating surfaces of shank portions 54 and 64 move across each other, layer 49 disposed on one or both of the opposing mating surfaces of the shank portions prevents electrical shorting between those surfaces. Thus, layer 49 electrically isolates shank portions 54 and 64 in the same manner that it electrically isolates shearing surfaces 50 and 60. Alternatively, layer 49 need not be be disposed on the interior surfaces of one or both shank portions 54 and 64, but may comprise an electrically insulating washer disposed, for example, on insulating drive pin 46 between shank portions 54 and 64, thereby separating the shank portions.

Referring again to FIG. 3, shank portions 54 and 64 of members 18 and 19 include angled slots 55 and 65. The exterior surfaces of shank portions 54 and 64 contact the interior surfaces of halves 16' at indentations 42. Since the interior surfaces of indentations 42 are not covered by insulating material 45, halves 16' are in direct electrical contact with shank portions 54 and 64.

Members 18 and 19 and drive rod halves 16' are constructed of a metallic material that provides good electrical contact, such that the sliding contact resistance of each member 18 and 19 and its respective drive rod halve 16' is less than 5 ohms, and preferably less than 1 ohm. The interior surfaces of indentations 42 and the exterior surfaces of shank portions 54 and 64 may be gold plated to reduce the sliding electrical contact resistance.

Accordingly, the electrical circuit energizing each bipolar electrode extends from electrical terminals 17 on the proximal portion 30 of drive rod 16, through halve 16' of drive rod 16 to proximal portion 31 of halve 16'. The outwardly disposed shank portion of the respective members 18 and 19 are in sliding electrical contact with the interior surfaces of indentations 42 of each of drive rod halves 16', thereby providing a voltage potential across the tissue contacting portions of working end 11. Insulating layer 45 (or insulating strip 73 of the embodiment of FIG. 4) electrically isolates halves 16' (or electrode halves 72), while layer 49 of insulating material on one or both of members 18 and 19 electrically isolates those members, as described heretofore.

Insulating drive pin 46 extends through slots 55 and 65 of shank portions 54 and 64. The ends of insulating drive pin 46 are disposed in apertures 47 of drive rod halves 16' so that they do not interfere with reciprocatory movement of drive rod 16 in elongated barrel 15. Insulating pin 46 may be comprised of, for example, silicon nitride, zirconia, alumina, or other material which has the mechanical strength to withstand the loads imposed on the pins during opening and closing of members 18 and 19, while providing the requisite electrical insulation between shank portions 54 and 64.

As shown in FIGS. 5A and 5B, slots 55 and 65 are configured so that when the handle members are actuated to urge drive rod 16 in a distal direction, insulating drive pin 46 is urged to the distal ends of slots 55 and 65, thereby opening members 18 and 19 (see FIG. 5A). In this first position, working end 11 may be positioned so that members 18 and 19 are located proximate to the tissue, without imposing any mechanical load thereon.

On the other hand, when handle members 12 and 13 are rotated towards each other, drive rod 16 is reciprocated proximally. This motion pulls drive pin 46 toward to the proximal ends of slots 55 and 65, thereby closing members 18 and 19 as shown in FIG. 5B. As members 18 and 19 are gradually closed, the cutting point defined by the intersection of cutting edges 51 and 61, moves along those cutting edges, so that a current flows through the tissue to cause hemostasis of the tissue immediately prior to its being severed mechanically. Thus, in this second position, hemostasis is achieved in the tissue by the current flowing between members 18 and 19, and then mechanically severed.

Layer 49 of electrically insulating material may have a hardness that is greater or substantially greater than the steel or other electrically conducting material used to manufacture conventional scissors-like devices. For example, members 18 and 19 may be made of a martensitic stainless steel, e.g., AISI 420. Insulating layer 49 may then comprise, for example, a ceramic material such as alumina or zirconia, that is deposited on shearing surface 52 of member 18 by conventional plasma or flame-sprayed deposition techniques. The applied coating forms a non-conductive cutting edge for that member and has a greater hardness than the steel substrate and the steel of opposing member 19. Consequently, as layer 49 rubs against the cutting edge 61 or shearing surface 60 of member 19, steel shearing surface 60 and cutting edge 61 are mechanically ground or polished by the harder insulating layer 49. Cutting edges 51 and 61 are therefore self-sharpening and remain sharp during continued use.

Insulating layer 49 has a thickness in the range of 0.002 inches to about 0.050 inches, more preferably 0.003 to 0.007 inches. The applicant has determined that at thicknesses 0.001 inch or less, the thickness of the insulating layer 49 is insufficient to prevent shorting of the electrodes. Insulating layer thicknesses above 0.002 inches and below 0.050 inches cause adequate hemostasis. It has been observed, however, that the greater the minimum distance between the proximate current conducting portions of the opposing electrodes in the region of current flow through the tissue, the longer the current path through the tissue and the more difficult it becomes to obtain the desired localized and intense heating to achieve adequate hemostasis. Insulating layer thicknesses above 0.050 inches are believed to be too large for most practical applications, for the ceramic insulating materials described.

Figure 6:
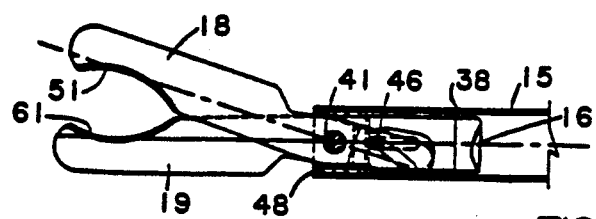
FIG. 6 is a cross-sectional view of an alternate embodiment of the scissors-like working end of the present invention.

FIG. 6 shows an alternative embodiment of the working end of FIGS. 5A and 5B, in which like numbers designate similar elements. The embodiment of FIG. 6 differs from that of FIGS. 5A-B chiefly in that the cutting edges 51 and 61 are curved rather than straight, and member 19 is fixed relative to the longitudinal axis of elongated barrel 15. Thus, reciprocatory movement of drive pin 46 moves member 18 between the open and closed positions. Curved cutting edges 51 and 61 ensure that the tissue to be severed does not slip from between members 18 and 19 during the cutting action, thereby providing enhanced precision in cutting tissue.

Referring now to FIGS. 7A and 7B, an alternate embodiment of working end 11 of the present invention is described, in which like-primed numbers designate similar elements. Jaw-like members 18' and 19' have shank portions 54' and 64' respectively Shank portions 54' and 64' in turn have angled slots 55' and 65' respectively. Insulated drive pin 46' extends through slots 55' and 65' and has its ends secured in apertures 47' of indentations 42'. Members 18' and 19' have grasping surfaces 50' and 60', teeth 51' and 61' and exterior surfaces 52' and 62', respectively. Teeth 51' and 61' are disposed in opposing relation on grasping surfaces 50' and 60' to grasp tissue captured between members 18' and 19'. Alternatively, the grasping surfaces may include a pattern of pyramidal teeth that serve to grasp the tissue.

As for the embodiment of FIGS. 5A and 5B, members 18' and 19' of the device of FIGS. 7A-B comprise the electrodes of a bipolar device. A thin layer 49' of insulation may be disposed on one or both of the mating surfaces of shank portions 54' and 64' to prevent electrical shorting between members 18' and 19' when those members are moved between the open and closed positions. Alternatively, layer 49' may comprise an insulating washer disposed on insulating drive pin 46 between the shank portions to electrically isolate shank portions 54' and 64'.

Layer 49' of insulating material may in addition cover the opposing surfaces of teeth 51' and 61' of the respective members. Alternatively, teeth 51' and 61' may be dimensioned so that when the members are in the closed position, a gap exists between teeth 51' and 61' sufficient to prevent direct shorting between the members.

Actuation of the handle members of the instrument urges drive pin 46' to move members 18' and 19' from a first position where the members can be disposed around a mass of tissue, to a second position where the members grasp the tissue. Members 18' and 19' therefore move through a graspers-like range of motion, similar to that of a conventional pliers. In the second position, current flows between members 18' and 19' to achieve hemostasis of the tissue captured therebetween.

Exterior surfaces 52' and 62' of members 18' and 19' may have a smooth, rounded, cross-section to facilitate blunt dissection. For example, such an instrument may be inserted—with members 18' and 19' closed together—into an incision made in a multilayer tissue mass. In this first position, the tissue merely contacts the outer surface of members 18' and 19', without imposing a substantial mechanical load thereon.

The electrodes may then be energized, and jaw-like members 18' and 19' may be gradually opened to separate the layers of tissue while simultaneously causing hemostasis of the tissue. When members 18' and 19' are moved to this second position, the outer surfaces of the members engage the tissue and separate the tissue layers along tissue boundaries without severing.

Figure 8:
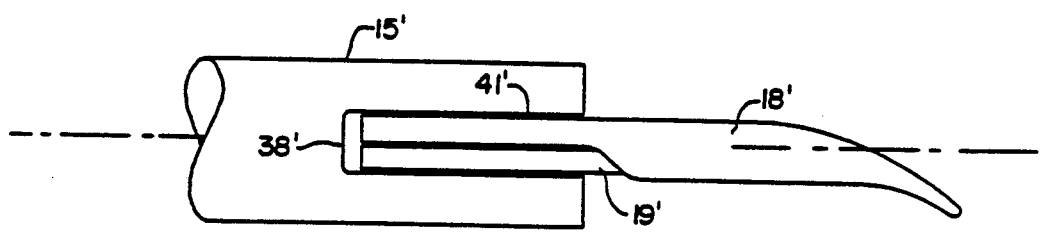
FIG. 8 is a plan view of an alternate embodiment of the dissector embodiment of the present invention.

FIG. 8 shows an alternative embodiment of the working end of FIG. 7, in which the tips of members 18' and 19' are curved so that they lie in a plane parallel to the longitudinal axis of elongated barrel 15'. Because the endoscope is typically inserted into the surgical area adjacent to the surgical instrument, the parallax resulting from the acute angle formed between the endoscope and the surgical instrument may restrict the surgeon's view of the surgical site. Thus, the surgeon may have only a limited view of the working end of the surgical instrument.

The embodiment of FIG. 8, however, resolves this difficulty by enhancing the surgeons's view of the working end of the instrument. Providing a curved working end, so that its tips lie in a plane parallel to the longitudinal axis of elongated barrel 15', enhances the precision of the surgical procedure. Of course, it will be apparent to one skilled in the art that any of the previously discussed embodiments of working end 11 of the present invention similarly could be provided with curved tips to enhance the surgeon's field of view. To ensure that the working end of the instrument will pass easily through standard trocar tubes, the tips of members 18' and 19' should not extend beyond the diameter of elongated barrel 15.

In addition to the above-described endoscopic bipolar instruments, the present invention includes use of such instruments in combination with a power supply providing a substantially constant voltage at selectable output levels, wherein the voltage output is independent of the load impedance. Such devices are described, for example, in U.S. Pat. Nos. 4,092,986 and 4,969,885.

To reduce coagulum buildup on the working surfaces of the scissors, applicant has developed power supplies providing substantially constant voltage output that is independent of the load impedance, low source impedance and a alternating-current voltage waveform having a crest factor—the ratio of peak voltage to RMS voltage—near unity. These power supplies are described in copending and commonly assigned U.S. patent application Ser. No. 07/877,703. The present invention, when powered by such experimental power supplies, has been observed to provide highly satisfactory hemostasis without arcing or charring of the tissue, and little coagulum buildup.

The present invention includes the method steps of employing an apparatus having movable members that include electrodes with an interposed layer of insulating material, wherein operation of the apparatus simultaneously manipulates and causes hemostasis of the tissue. Applicant has observed that use of apparatus constructed in accordance with the principles of this invention provides good results, with little sticking or coagulum accumulation, when used in conjunction with a power supply having a load-independent substantially constant voltage output. Frequencies in the range of 100 kHz to 2 MHz and voltages in the range of 10 to 120 volts (RMS) (across the bipolar electrodes) have been determined to provide highly satisfactory performance under a wide range of conditions.

The method of the present invention, suitable for use in performing a great variety of endoscopic surgical procedures on a patient's internal tissue, comprises the steps of:

(a) providing an instrument having an elongated barrel, actuating means, and a working end comprising first and second members movable between first and second positions, the first and second members having opposing mating surfaces that move across each other when the first and second members are moved between the first and second positions, each of the first and second members having an electrode associated therewith;

(b) providing an electrically insulating material between the first and second electrodes so that the electrodes do not contact each other when the opposing mating surfaces move across each other;

(c) connecting the electrodes to a power supply;

(d) incising the patient's tissue with a trocar or similar device to create a small opening into the patient's body cavity;

(e) inserting the working end and elongated barrel of the instrument through a trocar tube so that the working end is disposed adjacent to the internal tissue;

(f) selecting and maintaining a substantially constant voltage level output across the power supply, the voltage level output independent of the load impedance;

(g) placing the electrodes in electrical contact with the tissue; and (h) operating the actuating means to move the first and second members between the first and second positions to simultaneously manipulate the tissue and cause hemostasis of the tissue by passing a current therethrough.

Of course, it will be apparent to one skilled in the art that steps (a) and (b) described above can be combined by simply providing an apparatus as hereinbefore described. Operation of the apparatus in the range 10 to 90 volts (RMS) is desirable in many cases, depending upon the impedance of the tissue encountered during the surgical procedure. Of course, one skilled in the art will also recognize that the above-stated voltages are those imposed across the electrodes of the bipolar instrument, rather than the output terminals of the power supply, since allowance must be made for line losses encountered in the cables connecting the electrosurgical instrument to the power supply.

The use of a power supply having a selectable substantially constant voltage level output that is independent of load impedance provides sufficient power to cause effective hemostasis. Use of voltage output levels lower than those generally used in previously known electrosurgical instruments reduces the power delivered to the electrodes when they are not in contact with tissue, i.e., open-circuited, and reduces the likelihood of generating a current arc when the electrodes are brought into contact with the tissue.

Use of a constant voltage level output that is independent of the load impedance inhibits excessive current flow through the tissue, as the tissue resistance increases during desiccation. Consequently, the depth of hemostasis obtained within the tissue can be more precisely controlled, and localized overheating of the electrodes better avoided. Reduced localized heating of the electrodes also inhibits coagulum buildup, which can both interfere with efficient hemostasis and impede maneuverability of the instrument.

The various embodiments described herein are presented for purposes of illustration and not limitation, as the present invention can be practiced with endoscopic surgical instruments of any type having two opposing members movable with respect to one another. The instruments and methods of the present invention may be adapted, as may be required, for use in operating on any internal tissue, vessel, or organ.

For example, the present invention may be practiced using an actuating means comprising a pistol style grip having a spring-biased trigger to reciprocate drive rod 16, rather than the handle members described hereinbefore. One skilled in the art will appreciate that the present invention can be practiced by other than the described embodiments, and that the present invention is limited only by the claims that follow.

What is claimed is:

1. An instrument for performing endoscopic electrosurgery on a tissue by passing a current through the tissue to cause hemostasis thereof, the instrument comprising:

an elongated barrel having a proximal end and a distal end;

first and second shearing members disposed on the distal end of the elongated barrel, the first shearing member having a first shearing surface, a first cutting edge having a length and a first exterior surface, a portion of the first exterior surface adjacent the first cutting edge defining a first electrode;

the second shearing member having a second shearing surface, a second cutting edge, and a second exterior surface, a portion of the second shearing member adjacent the second cutting edge defining a second electrode;

means for connecting the first and second shearing members so that the first shearing surface moves relative to the second shearing surface through a range of motion in a scissors-like cutting action, wherein the first and second cutting edges close together for shearing tissue located therebetween the scissor-like cutting action defining a cutting point located just distally of where the first and second cutting edges come together, the cutting point moving distally along the cutting edges where the first and second cutting edges come together through the range of motion; and an electrically insulative material interposed between the first and second electrodes so that the first and second electrodes do not contact each other in the range of motion, and so that the current passes between the first and second electrodes distal to the cutting point and not between the first and second shearing surfaces, the first and second cutting edges cutting the tissue at the cutting point; and actuating means connected to the proximal end of the elongated barrel to move the first and second shearing members through the range of motion, wherein the first and second shearing members comprise an electrically conductive material, the means for connecting the first and second shearing members comprises a material that does not conduct electricity between the first and second shearing members and the electrically insulative material comprises a first layer of material disposed on the first shearing member to form substantially the entire length of the first cutting edge and the first shearing surface.

2. An instrument as defined in claim 6 wherein the actuating means comprises first and second handle members and means for fastening the first and second handle members together for relative movement.

3. The instrument as defined in claim 6 wherein the elongated barrel has a longitudinal axis, the first and second shearing members have first and second tips, and the first and second shearing members are curved so that the first and second tips lie in a plane parallel to and separated from the longitudinal axis of the elongated barrel.

4. An instrument as defined in claim 1 wherein at least one of the first and second cutting edges is curved.

5. An instrument as defined in claim 1 wherein the first layer of electrically insulative material has a first hardness, the second shearing member has a second hardness, and the first hardness is greater than the second hardness.

6. An instrument as defined in claim 1 wherein the first layer has a thickness selected in the range of 0.002 to 0.050 inches.

7. An instrument as defined in claim 1 wherein the first layer has a thickness selected in the range of 0.003 to 0.007 inches.

8. An instrument as defined in claim 1 further comprising a second layer of electrically insulative material disposed on the second shearing member to form the second cutting edge and the second shearing surface.

9. An instrument as defined in claim 8 wherein the first layer has a first thickness and the second layer has a second thickness and the sum of the first and second thicknesses is in the range of 0.002 and 0.050 inches.

10. An instrument as defined in claim 9 wherein the sum of the first and second thicknesses is in the range of 0.003 to 0.007 inches.

11. The instrument of claim 1, wherein the instrument has a load impedance, in combination with a power supply that provides a high frequency alternating-current waveform, the power supply having a selectable substantially constant voltage level output that is independent of the load impedance, and means for electrically connecting the power supply to the first and second electrodes.

12. The apparatus of claim 11 wherein the substantially constant voltage level output of the power supply is selectable to provide a voltage across the first and second electrodes from the range of 10 to 120 volts RMS.

13. The apparatus of claim 11 wherein the power supply provides a voltage waveform having a crest factor near unity.

14. The apparatus of claim 11 wherein the power supply provides an alternating-current voltage waveform having a high frequency selected from the range of 100 kHz to 2 MHz.

15. An instrument for performing endoscopic electrosurgery on a tissue by passing a current through the tissue to cause hemostasis thereof, the instrument comprising:

an elongated barrel having a proximal end and a distal end;

first and second grasping members disposed on the distal end of the elongated barrel, the first and second grasping members including shank portions having opposing mating surfaces, each of the shank portions having a longitudinally directed slot, the first grasping member having a first grasping surface, and a first exterior surface, a portion of the first exterior surface adjacent the first grasping surface defining a first electrode;

the second grasping member having a second grasping surface, and a second exterior surface, a portion of the second grasping member adjacent the second grasping surface defining a second electrode;

means for connecting the first and second grasping members so that the first and second grasping surfaces move through a range of motion in a graspers-like action to grasp tissue disposed therebetween, the shank portions moving across each other as the first and second grasping surfaces move through the range of motion;

a pin extending through the slots in the shank portions, the pin adapted for reciprocation in proximal and distal directions;

an electrically insulative material disposed on at least one of the first and second grasping members to form the grasping surface of that grasping member, so that the first and second electrodes do not contact each other in the range of motion, and so that the current passes between the first and second electrodes through the tissue and not between the first and second grasping surfaces, the electrically insulative material interposed between the shank portions so that a leakage current does not pass between the shank portions; and actuating means connected to the pin to move the first and second grasping members through the range of motion.

16. An instrument as defined in claim 15 wherein the first and second grasping members are made of an electrically conductive material.

17. The instrument as defined in claim 15 further comprising portions of the first and second grasping surfaces defining serrations or a pyramidal array of grasping the tissue.

18. An instrument as defined in claim 15 wherein the electrically insulative material comprises a layer disposed on at least one of the mating surfaces of the shank portions.

19. An instrument as defined in claim 15 wherein the electrically insulative material comprises an insulating washer interposed between the mating surfaces of the shank portions to electrically isolate the shank portions.

20. An instrument as defined in claim 15 for performing endoscopic electrosurgery wherein layers of tissue are hemostatically separated, wherein the first and second grasping members are closed together and inserted into the tissue, and the actuating means, when operated, cause the first and second grasping members to open, thereby separating the layers of tissue while simultaneously achieving hemostasis by passing current through the layers of tissue and between the first and second electrodes.

21. The instrument as defined in claim 20 wherein the elongated barrel has a longitudinal axis, the first and second grasping members have first and second tips, and the first and second grasping members are curved so that the first and second tips lie in a plane parallel to and separated from the longitudinal axis of the elongated barrel.

22. An instrument for performing endoscopic electrosurgery on a tissue by passing a current through the tissue to cause hemostasis thereof, the instrument comprising:

an elongated barrel having a proximal end and a distal end;

first and second shearing members disposed on the distal end of the elongated barrel, the first shearing member comprising an electrically non-conductive material, the first shearing member having a first shearing surface, a first cutting edge having a length and a first exterior surface, the non-conductive material extending along substantially the entire length of the first cutting edge;

the second shearing member comprising an electrically non-conductive material, the second shearing member having a second shearing surface, a second cutting edge, and a second exterior surface;

means for connecting the first and second shearing members so that the first shearing surface moves relative to the second shearing surface through a range of motion in a scissors-like cutting action, wherein the first and second cutting edges close together for shearing tissue located therebetween, the scissor-like cutting action defining a cutting point located just distally of where the first and second cutting edges come together, the cutting point moving distally along the cutting edges where the first and second cutting edges come together through the range of motion; and first and second electrodes disposed on the first and second shearing members, respectively, the first electrode comprising a first layer of electrically conductive material disposed on the first exterior surface and the second electrode comprising a second layer of electrically conductive material disposed on the second exterior surface so that the first and second electrodes do not contact each other in the range of motion, and so that the current passes between the first and second electrodes distal to the cutting point and not between the first and second shearing surfaces, the first and second cutting edges cutting the tissue at the cutting point; and actuating means connected to the proximal end of the elongated barrel to move the first and second shearing members through the range of motion.

23. An instrument as defined in claim 22 wherein the first and second layers are spaced apart, at the cutting point, a distance in the range of 0.002 to 0.050 inches, as the cutting point moves through the range of motion.

24. The instrument of claim 22, wherein the instrument has a load impedance, in combination with a power supply that provides a high frequency alternating-current waveform, the power supply having a selectable substantially constant voltage level output that is independent of the load impedance, and means for electrically connecting the power supply to the first and second electrodes.

25. The apparatus of claim 24 wherein the substantially constant voltage level output of the power supply is selectable to provide a voltage across the first and second electrodes from the range of 10 to 120 volts RMS.

26. The apparatus of claim 24 wherein the power supply provides a voltage waveform having a crest factor near unity.

27. The apparatus of claim 24 wherein the power supply provides an alternating-current voltage waveform having a high frequency selected from the range of 100 kHz to 2 MHz.

* * * * *

UNITED STATES PATENT AND TRADEMARK OFFICE
CERTIFICATE OF CORRECTION

PATENT NO. : 5,330,471
DATED : July 19, 1994
INVENTOR(S) : Philip E. Eggers

It is certified that error appears in the above-indentified patent and that said Letters Patent is hereby corrected as shown below:

| Column | Line | |
|--------|------|---|
| 9  | 4  | after "07/877,703", insert --,-- |
| 11 | 36 | after "respectively", insert --.-- |
| 15 | 14 | change "6" to --1-- |
| 15 | 18 | change "6" to --1-- |
| 16 | 51 | change "of" to --for-- |

Signed and Sealed this

Twenty-seventh Day of August, 1996

Attest:

BRUCE LEHMAN

*Attesting Officer*  *Commissioner of Patents and Trademarks*